(12) United States Patent
Langlais et al.

(10) Patent No.: US 8,549,928 B2
(45) Date of Patent: Oct. 8, 2013

(54) WELD STRENGTH TEST

(75) Inventors: Michael Dean Langlais, Houston, TX (US); Evgeny Anikanov, The Woodlands, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 61 days.

(21) Appl. No.: 13/309,172

(22) Filed: Dec. 1, 2011

(65) Prior Publication Data

US 2013/0055824 A1    Mar. 7, 2013

Related U.S. Application Data

(60) Provisional application No. 61/531,663, filed on Sep. 7, 2011.

(51) Int. Cl.
     *G01N 17/00*      (2006.01)
     *G01N 3/20*      (2006.01)

(52) U.S. Cl.
     USPC .......................... 73/850; 73/150 A; 73/150 R (58) Field of Classification Search
     USPC ............. 73/850, 115 R, 115 A, 150 R, 150 A
     See application file for complete search history.

(56) References Cited

U.S. PATENT DOCUMENTS

| | | | |
|---|---|---|---|
| 4,358,961 | A | 11/1982 | Woods, Jr. |
| 5,191,720 | A | 3/1993 | Miura et al. |
| 5,587,537 | A | 12/1996 | Simmons |
| 5,597,959 | A * | 1/1997 | Rice et al. ........................ 73/850 |
| 2010/0019785 | A1 | 1/2010 | Wang et al. |

OTHER PUBLICATIONS

International Search Report and Written Opinion issued in PCT/US2012/052988 on Nov. 16, 2012, 10 pages.

* cited by examiner

*Primary Examiner* — Lisa Caputo
*Assistant Examiner* — Jonathan Dunlap
(74) *Attorney, Agent, or Firm* — David G. Matthews; Bryan White; Brandon Clark (57) ABSTRACT

A push test fixture having a cradle and a load pin is provided along with a test sample that reasonably represents the strength and quality of the original welds that hold the wrap wires and axial wires of the sample together. The test sample is placed in the push test fixture such that a particular weld on the test sample is aligned between the cradle and the load pin. A load is applied through the weld using the load pin, and a strength property such as the ultimate strength or the yield strength of the weld is determined. The cradle helps maintain the original, as-wrapped curvature of the wrap wire. The test samples can come, for example, from direct wrap filters or wire-wrap jackets. The strength property can be determined for at least every third wrap wire of the test sample.

24 Claims, 6 Drawing Sheets

UN-RESTRAINED REGION

FIG. 9

MOMENT ARM LENGTH

WELD STRENGTH TEST

RELATED APPLICATIONS

This application claims the benefit of a related U.S. Provisional Application Ser. No. 61/531,663 filed Sep. 7, 2011, entitled "Weld Strength Test," to Langlais, et al., the disclosure of which is incorporated by reference herein in its entirety.

BACKGROUND

The production of formation sand into a well is a problem when producing, for example, oil or gas, because of its adverse effects on well productivity and equipment. The produced sand often originates from shallow, geologically young formations that have little or no natural cementation to hold the individual sand grains together. As a result, when the wellbore pressure is lower than the reservoir pressure, drag forces are applied to the formation sands as formation fluid is produced. If the formation's restraining forces are exceeded, sand will be drawn into the wellbore.

Operational problems that can arise if a well produces sand include, but are not limited to, erosion of surface equipment, casing or tubular damage, and loss of productivity. Thus, various production and completion practices have been developed to avoid excess sand production. For example, mechanical retention may be used to prevent sand from entering the wellbore flow stream. Mechanical retention relies on sand bridging. That is, certain material is retained to prevent other material from entering the wellbore. Retention of larger particles causes smaller particles to bridge behind them.

One type of device used to restrict sand movement is referred to as a screen. A screen often used in conjunction with a mechanical sand-control technique known as "gravel-packing". Gravel packing involves running a mechanical device such as a screen into the well and placing accurately sized "gravel" around the screen. The gravel comprises large, clean sand particles. ("Large" refers to its particle size relative to the formation sand particle size.) Such placement of gravel allows the passage of fluids through the gravel and screen, but prevents passage of formation sand into the wellbore flow stream.

SUMMARY

A push test fixture having a cradle and a load pin is provided along with a test sample that reasonably represents the strength and quality of the original welds that hold the wrap wires and axial wires of the sample together. The test sample is placed in the push test fixture such that a particular weld on the test sample is aligned between the cradle and the load pin. A load is applied through the weld using the load pin, and a strength property such as the ultimate strength or the yield strength of the weld is determined. The cradle helps maintain the original, as-wrapped curvature of the wrap wire. The test samples can come, for example, from direct wrap filters or wire-wrap jackets. The strength property can be determined for at least every third wrap wire of the test sample. This summary is provided to introduce a selection of concepts that are further described below in the detailed description. This summary is not intended to identify key or essential features of the claimed subject matter, nor is it intended to be used as an aid in limiting the scope of the claimed subject matter.

FIGURES

Embodiments of testing weld strength are described with reference to the following figures. The same numbers are used throughout the figures to reference like features and components.

It should be understood that the drawings are not to scale and that the disclosed embodiments are sometimes illustrated diagrammatically and in partial views. In certain instances, details that are not necessary for an understanding of the disclosed method and apparatus or that would render other details difficult to perceive may have been omitted. It should be understood that this disclosure is not limited to the particular embodiments illustrated herein.

DETAILED DESCRIPTION

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate.

A new weld strength test has been developed. This test, the "push" test, may not only reduce the compromising of sample integrity caused by sample preparation, but may also lessen premature weld failure due to the sample bending under the applied test load. In one embodiment, an applied force pushes the wrap wire from the axial wire instead of pulling the two wires apart. The wrap wire's outer edges (i.e., filtration edges) are not exposed when performing the push test. The push test loads the wrap wire from its underside.

Figure 1:
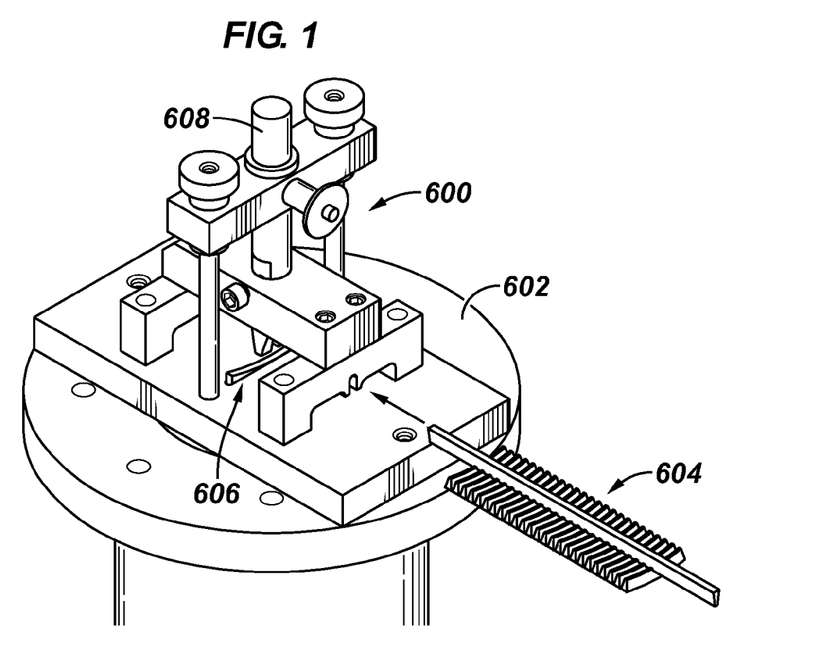
FIG. 1 schematically shows a push test fixture and stand with a direct wrap screen sample ready to be inserted into the push test fixture, in accordance with the present disclosure.
Figure 2:
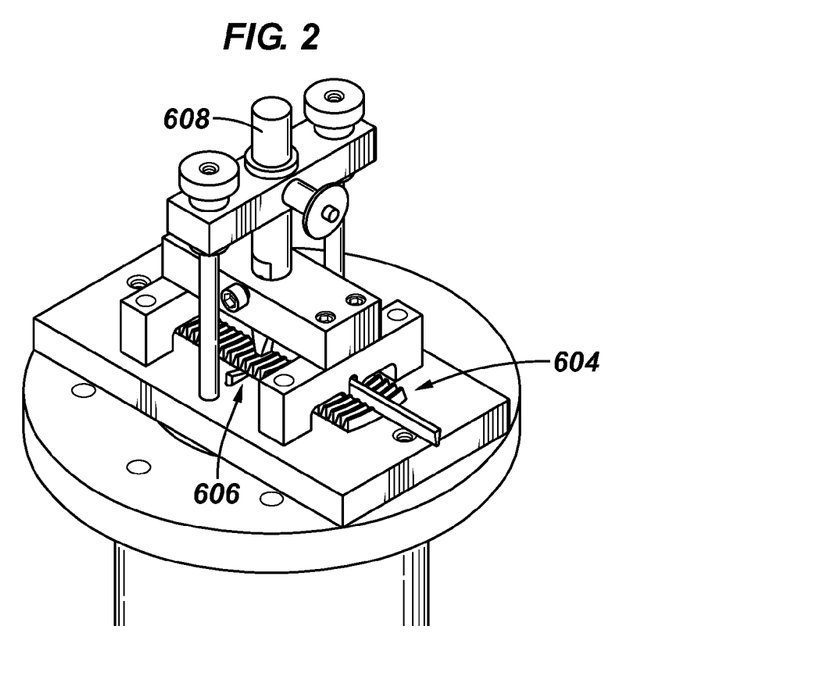
FIG. 2 schematically shows the push test fixture of FIG. 1 with the direct wrap screen sample of FIG. 1 properly inserted into the push test fixture, in accordance with the present disclosure.
Figure 3:
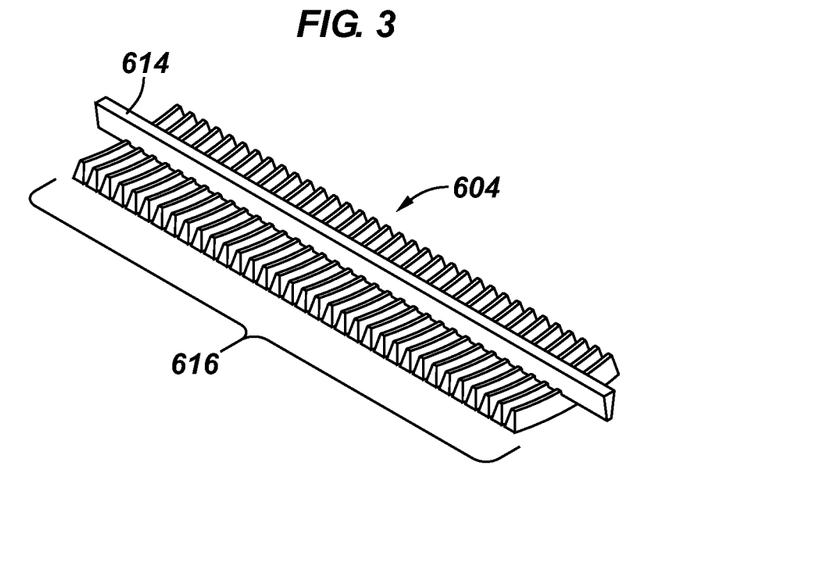
FIG. 3 shows a direct wrap test sample prepared in accordance with the present disclosure.

The new weld strength test may be applied, for example, to a direct wrap filter (screen) or a wire-wrap jacket. The term "wire-wrap sand screen", as used herein, refers to and encompasses at least the direct wrap screen and the wire-wrap jacket. For a direct wrap screen, the test may employs a calibrated compressive load tester with, for example, a minimum rating of 2000 lbf (8.9 kN). A push test fixture 600 is mounted on a stand 602 as shown in FIG. 1. Samples from the direct wrap screen may be chosen from approximately equal spaced locations, in an angular sense. In that case, three strips from approximately 120 degree offset locations are cut from the direct wrap filter. Each strip should be approximately one foot (300 mm) long, with the wrap wires attached to the axial wire, as shown in FIGS. 1, 2, and 3. Note, the last two wires on either end of the axial wire sample are not good test candidates. Traceability can be maintained by grouping the samples with tape or by placing the samples in a bag and labeling each group of samples with the orientation/heat/lot traceability information.

Figure 4:
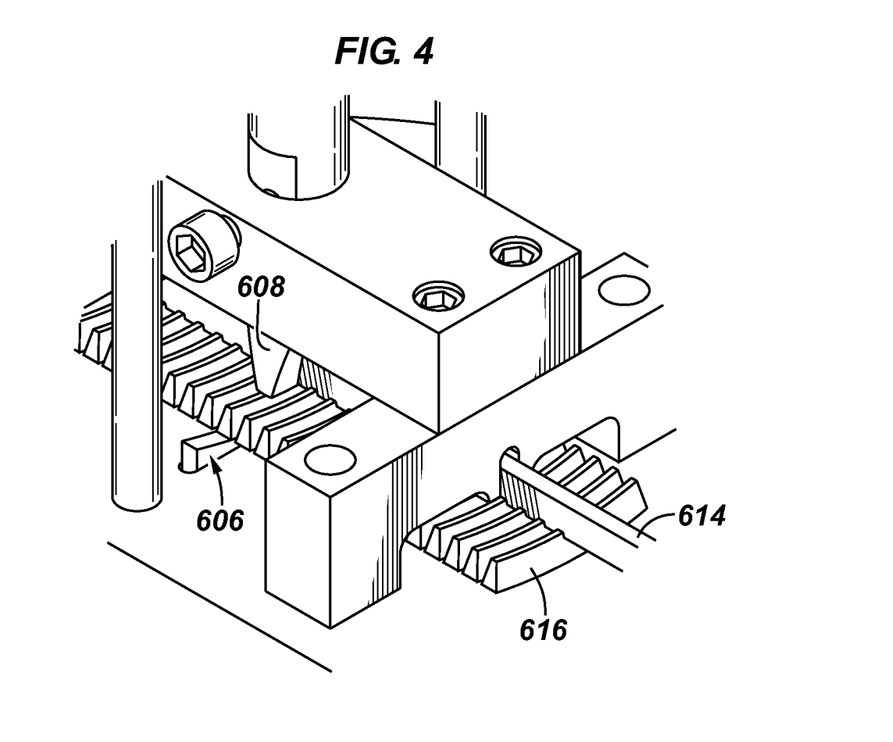
FIG. 4 schematically shows an enlarged view of the direct wrap screen sample of FIG. 2 properly aligned in the push test fixture, in accordance with the present disclosure.
Figure 5:
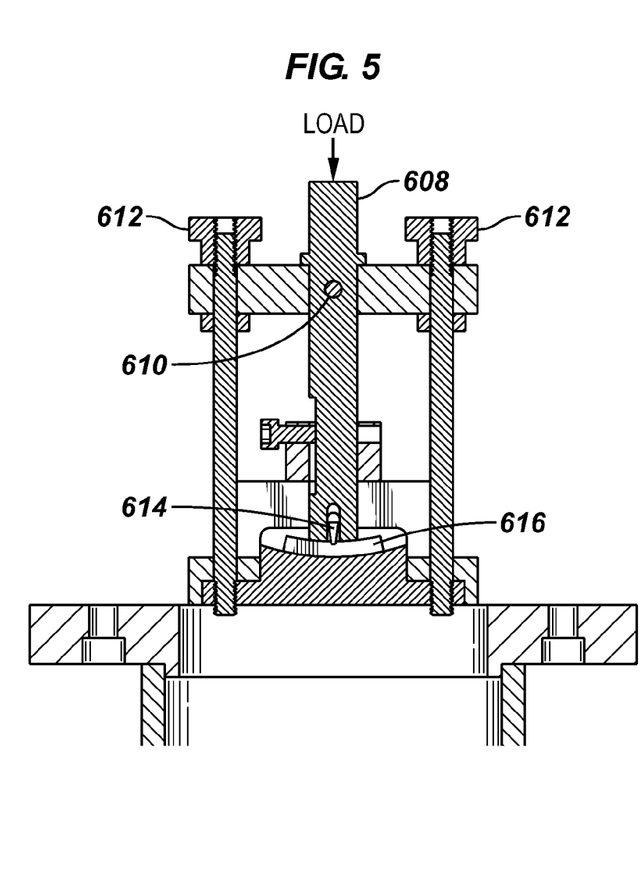
FIG. 5 schematically shows a push test fixture with a direct wrap screen sample inserted and aligned in the push test fixture and the push test fixture being in a first position, in accordance with the present disclosure.

The test sample strip 604 is insert into the load fixture through one end (see FIGS. 1 and 2). The wrap wire to be tested is positioned directly above the cradle 606, which also places the sample directly below a load pin 608 (see FIG. 4). The wrap wire being tested is supported in a cradle 606 to maintain the wrap wire's "as-wrapped" shape. A quick-release pin 610 is installed and two thumb screws 612 are tightened firmly to compress the wrap wire between the load pin 608 and the cradle 606 (see e.g., FIG. 5). The load tests are performed and the data is recorded. Note that within a single strip it is possible to load test every third wrap wire and obtain valid test results.

Figure 6:
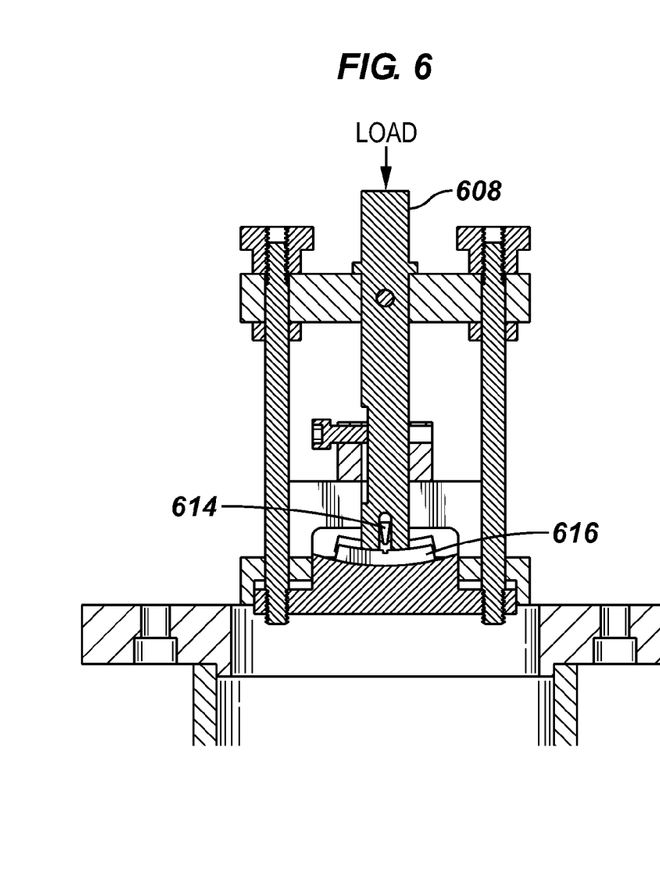
FIG. 6 schematically shows the push test fixture of FIG. 5 with the direct wrap screen sample of FIG. 5 inserted and aligned in the push test fixture and the push test fixture being in a second position, in accordance with the present disclosure.

Once assembled, the components described above and shown in FIGS. 5 and 6 move as a unit that focuses the applied load directly to the weld between the axial wire and wrap wire. FIG. 6 shows separation of the axial wire 614 and the wrap wire 616 being tested.

To minimize sample manipulation, the wrap wires 616 are cut proximal to the axial wires flanking the particular axial wire 614 to be tested. Because there is no removal of wrap wires as for the pull test, the integrity of the wrap wire to axial wire weld is not compromised. From this sample it is possible to test every third wrap wire weld, enabling an additional number of tests per sample. In the push test, the wrap wire sample is cradled or supported the entire time the test load is applied. That is, the trapping of the wrap wire between the cradle and load pin applying the test load helps maintain the wrap wire's "as-wrapped" shape throughout the test procedure, thereby ensuring the tested weld is not prematurely weakened.

Figure 7:
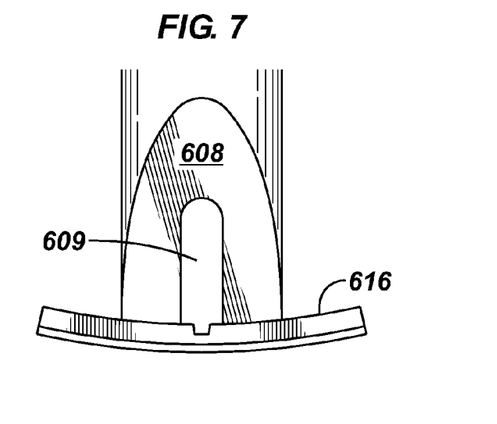
FIG. 7 shows an enlarged view of a load pin pressing on a wire-wrap sample, in accordance with the present disclosure.
Figure 8:
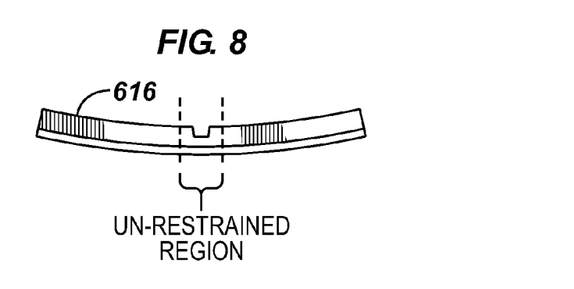
FIG. 8 shows the wire-wrap sample of FIG. 7 after being subjected to a push test, in accordance with the present disclosure.
Figure 9:
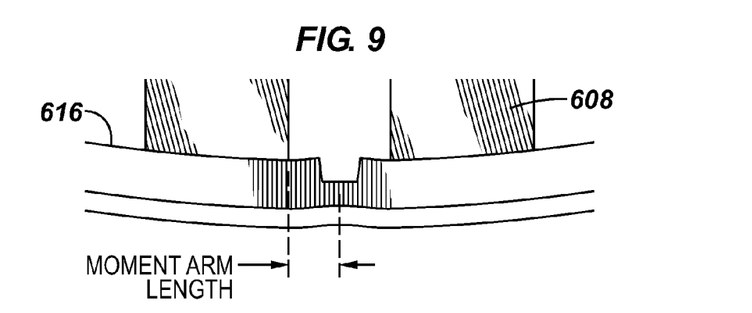
FIG. 9 shows an enlarged view of the wire-wrap sample of FIG. 8.

The push test, by compressing the wrap wire between the cradle and load pin, reduces the "peeling" effect, and thereby allows a greater percentage of the weld to contribute to the measured peak strength. The high clamping force between the load pin 608 and the cradle 606 prevents any lateral sliding movement of the sample 604. However, due to the axial wire clearance slot in the load pin 608, the wrap wire 616 is still able to bend within this non-compressed region (see FIGS. 7 and 8). The load pin 608 straddles the axial wire 614 resulting in a short, un-restrained region that is permitted to bend. The distance between the weld center point and the start of the load pin edge constitutes a short moment arm. However, with such a short moment arm, it takes significantly more force to bend the wrap wire. Unless the bending deformation during loading is completely eliminated, there will be a portion of the weld area that is prematurely weakened and will therefore not contribute to the measured strength property. To eliminate the bending completely, the wrap wire 616 and the axial wire 614 should be fully restrained through the loading point (i.e., directly above and below the weld). FIG. 9 shows a close up of the curvature of the wrap wire 616. Notice the localized arch below the weld point in the un-restrained region.

A similar test can be employed for a wire-wrap jacket. The test may employ a calibrated compressive load tester with, for example, a minimum rating of 800 lbf (3.55 kN). The push test fixture 600 is again mounted on a stand 602. Three axial wire strips are again cut from locations approximately 120 degrees from the wire-wrap jacket. It should be understood that more or fewer strips could be used. Each strip should comprise about one inch (25 mm) of axial wire with a minimum of ten wrap wires attached. The wrapping machine operator should select a particular axial wire and a wrap wire combination and document, for example, the heat number/PO number, operator, and wrapping machine on the sample container. The wrapping machine operator should cut approximately three inches (76 mm) from one end of the screen for the test.

Figure 10:
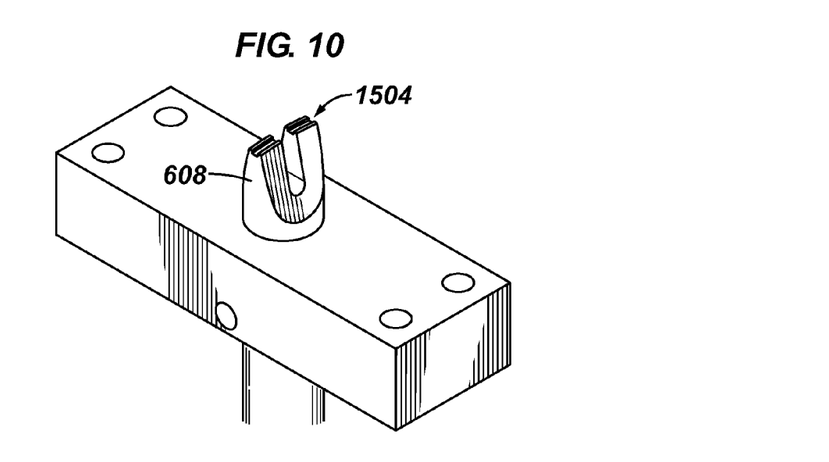
FIG. 10 shows the groove in the tip of the load pin of the push test fixture of FIG. 6, in accordance with the present disclosure.

The test sample 604 is placed into the push test fixture 600. The top part of the push test fixture 600 is placed onto the base plate, aligning dowel pins with holes in the push test fixture base. At the same time, the position of the sample is adjusted so that the small groove 1504 on the end of the load pin 608 rests directly on the weld tip of a wrap wire. FIG. 10 shows the small groove 1504 on the end of load pin 608.

With the test sample 604 placed in the push test fixture 600 so the load pin 608 is directly in line with the load tester push rod, an increasing load is applied to the test sample 604 until the sample yields or breaks. The test result (e.g., load at which sample yields or breaks) is recorded. The test is repeated for each subsequent sample. Within a single strip it is possible to load test every third wrap wire and obtain valid test results.

Figure 11:
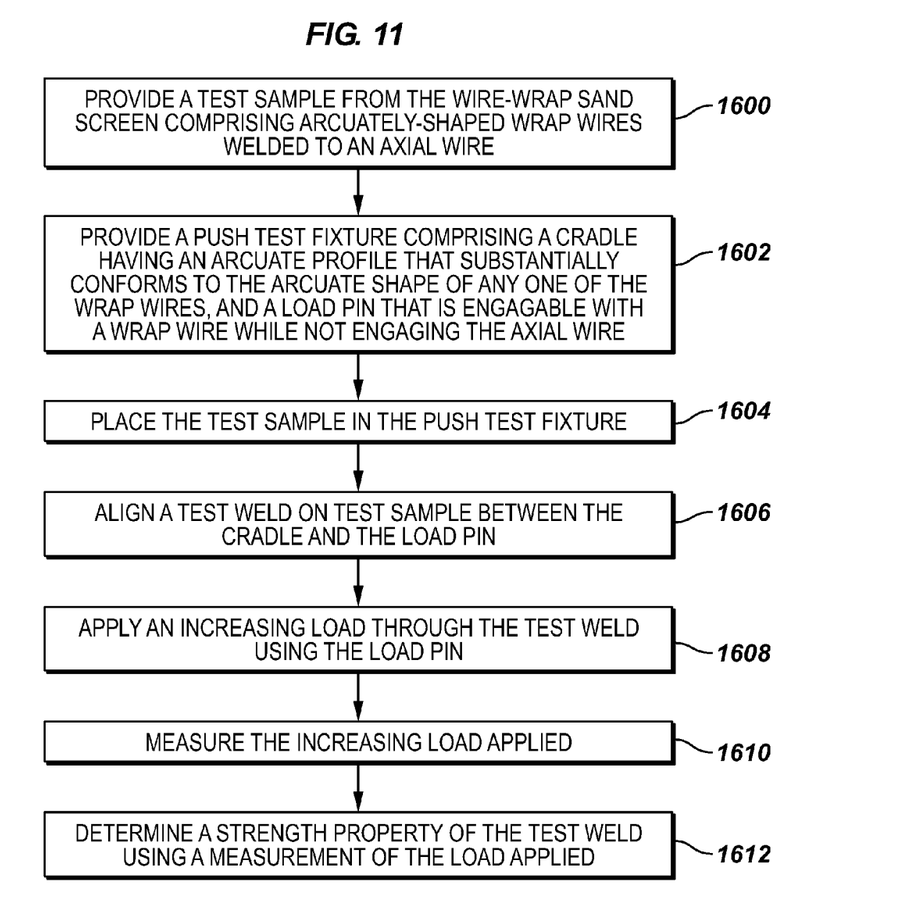
FIG. 11 is a flowchart showing an embodiment in accordance with the present disclosure.

In one embodiment, testing the strength of a weld on a sand screen may be done as follows and shown in the flowchart of FIG. 11:
providing a test sample from the wire-wrap sand screen comprising arcuately-shaped wrap wires welded to an axial wire (1600);
providing a push test fixture comprising a cradle having an arcuate profile that substantially conforms to the arcuate shape of any one of the wrap wires, and a load pin that is engagable with a wrap wire while not engaging the axial wire (1602);
placing the test sample in the push test fixture (1604);
aligning a test weld on test sample between the cradle and the load pin (1606);
applying an increasing load through the test weld using the load pin (1608);
measuring the increasing load applied (1610); and
determining a strength property of the test weld using a measurement of the load applied (1612).

Figure 12:
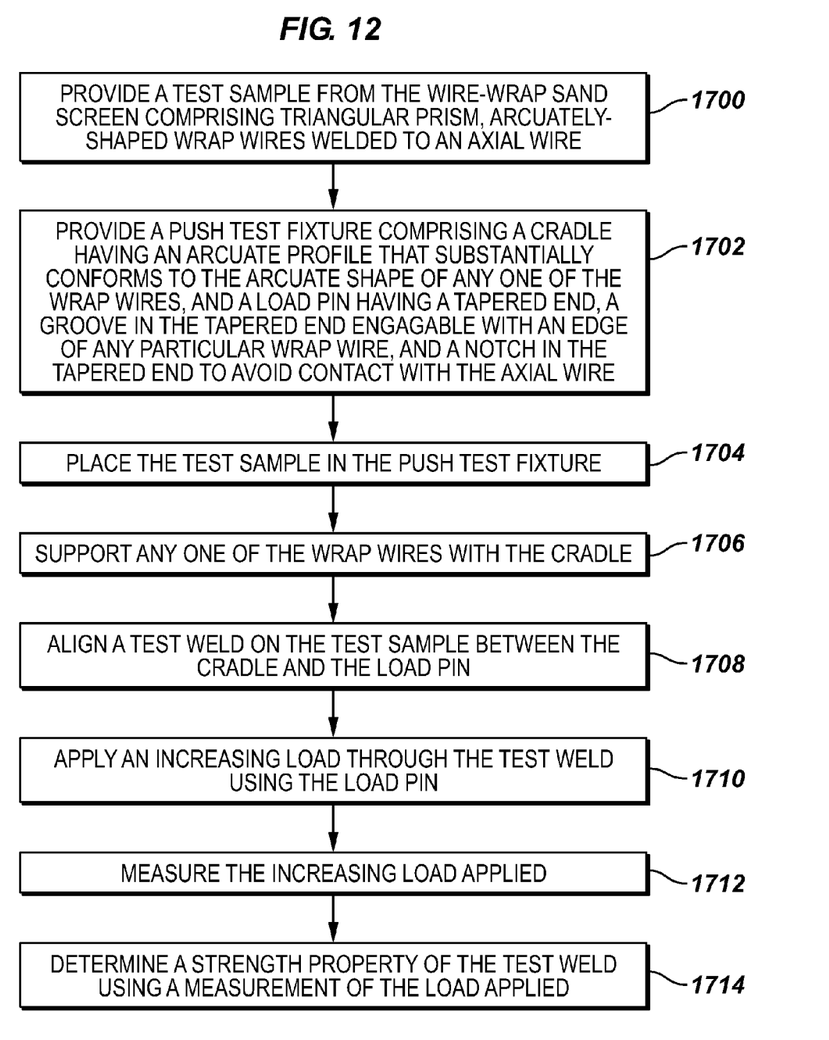
FIG. 12 is a flowchart showing an embodiment in accordance with the present disclosure.

In another embodiment, testing the strength of a weld on a sand screen may be done as follows and shown in the flowchart of FIG. 12:

providing a test sample from the wire-wrap sand screen comprising triangular prism, arcuately-shaped wrap wires welded to an axial wire (1700);
providing a push test fixture comprising a cradle having an arcuate profile that substantially conforms to the arcuate shape of any one of the wrap wires, and a load pin having a tapered end, a groove in the tapered end engageable with an edge of any particular wrap wire, and a notch in the tapered end to avoid contact with the axial wire (1702);
placing the test sample in the push test fixture (1704);
supporting any one of the wrap wires with the cradle (1706);
aligning a test weld on the test sample between the cradle and the load pin (1708);
applying an increasing load through the test weld using the load pin (1710);
measuring the increasing load applied (1712); and
determining a strength property of the test weld using a measurement of the load applied (1714).

In the embodiment shown, the load pin 608 is a single rod having a tapered end in which a groove 1504 is machined. The groove engages an edge of the triangular prism shaped wrap wire 616. Note, neither that particular shape of wrap wire nor the complementary groove is required. Load pin 608 also has a notch to provide clearance for the axial wire 614. Many alternate embodiments are possible that allow load pin 608 to apply a force on a wrap wire 616 without applying a contact load on axial wire 614. As stated above, the notch in the shown embodiments allows load pin 608 to straddle axial wire 614. As an example of a possible alternative design, two separate load pins working in conjunction with one another could be positioned on either side of the axial wire 614 to apply the desired load to the wrap wire 616.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method to test the strength of a weld on a wire-wrap sand screen, comprising:
  providing a test sample from the wire-wrap sand screen comprising arcuately-shaped wrap wires welded to an axial wire;
  providing a push test fixture comprising a cradle having an arcuate profile that substantially conforms to the arcuate shape of any one of the wrap wires, and a load pin that is engageable with a wrap wire while not engaging the axial wire;
  placing the test sample in the push test fixture;
  aligning a test weld on the test sample between the cradle and the load pin;
  applying an increasing load through the test weld using the load pin;
  measuring the increasing load applied; and
  determining a strength property of the test weld using a measurement of the load applied.

2. The method of claim 1, further including applying the increasing load until there is a failure of the test weld, and wherein determining the strength property of the weld corresponds to the load applied substantially at the time of the failure of the test weld.

3. The method of claim 2, wherein the failure of the test weld occurs when the wrap wire substantially separates from the axial wire.

4. The method of claim 1, further including applying the increasing load up to a predetermined load requirement, and wherein the test sample passes a minimum requirement if the test weld does not fail prior to the applied load reaching the predetermined load requirement.

5. The method of claim 1, wherein the load pin has a first contact area for contacting a portion of the wrap wire extending from the test weld on a first side of the axial wire and a second contact area for contacting a portion of the wrap wire extending from the test weld on a second side of the axial wire, and wherein the load pin applies the load to the wrap wire on opposite sides of the axial wire.

6. The method of claim 1, wherein the wherein the cradle supports any particular wrap wire.

7. The method of claim 6, further comprising maintaining the as-wrapped curvature of the wrap wire supported by the cradle.

8. The method of claim 1, wherein the strength property is selected from a group consisting of ultimate strength and yield strength.

9. The method of claim 1, further comprising recording the determined strength property.

10. The method of claim 1, further comprising determining the strength property for every third wrap wire of the arcuately-shaped wrap wires.

11. The method of claim 1, wherein the test sample is selected from a group consisting of direct wrap filters and wire-wrap jackets.

12. The method of claim 1, wherein the arcuate profile of the cradle contacts an outer radial surface of the wrap wire having the test weld while the load is applied to the test weld.

13. A method to test the strength of a weld on a wire-wrap sand screen, comprising:
  providing a test sample from the wire-wrap sand screen comprising triangular prism, arcuately-shaped wrap wires welded to an axial wire;
  providing a push test fixture comprising a cradle having an arcuate profile that substantially conforms to the arcuate shape of any one of the wrap wires, and a load pin having a tapered end, a groove in the tapered end engageable with an edge of any particular wrap wire, and a notch in the tapered end to avoid contact with the axial wire;
  placing the test sample in the push test fixture;
  supporting any one of the wrap wires with the cradle;
  aligning a test weld on the test sample between the cradle and the load pin;
  applying an increasing load through the test weld using the load pin;
  measuring the increasing load applied; and
  determining a strength property of the test weld using a measurement of the load applied.

14. The method of claim 13, wherein the providing a test sample comprises cutting the wrap wires proximal to axial wires flanking the axial wire.

15. The method of claim 13, wherein the strength property is selected from a group consisting of ultimate strength and yield strength.

16. The method of claim 13, further comprising approving corresponding screens for use based on the determined strength property.

17. The method of claim 13, further including applying the increasing load until there is a failure of the test weld, and wherein determining the strength property of the weld corresponds to the load applied substantially at the time of the failure of the test weld.

18. The method of claim 17, wherein the failure of the test weld occurs when the wrap wire substantially separates from the axial wire.

19. The method of claim 13, further including applying the increasing load up to a predetermined load requirement, and wherein the test sample passes a minimum requirement if the test weld does not fail prior to the applied load reaching the predetermined load requirement.

20. The method of claim 13, wherein the load pin has a first contact area on the tapered end for contacting a portion of the wrap wire extending from the test weld on a first side of the axial wire and a second contact area on the tapered end for contacting a portion of the wrap wire extending from the test weld on a second side of the axial wire, and wherein the load pin applies the load to the wrap wire on opposite sides of the axial wire.

21. The method of claim 13, wherein the arcuate profile of the cradle contacts an outer radial surface of the wrap wire having the test weld while the load is applied to the test weld.

22. A system to test the strength of a weld on a wire-wrap sand screen, comprising:
a push test fixture for testing a sample from the sand screen having arcuately-shaped wrap wires welded to an axial wire comprising a cradle having an arcuate profile that substantially conforms to the arcuate shape of any one of the wrap wires, and a load pin that is engagable with a wrap wire while not engaging the axial wire.

23. The system of claim 22, wherein the load pin has a groove on one end that engages an edge of any particular wrap wire.

24. The system of claim 22, wherein the load pin has a notch on one end.

* * * * *